United States Patent [19]

Schmitt et al.

[11] Patent Number: 5,277,589
[45] Date of Patent: Jan. 11, 1994

[54] PROCESS FOR THE DETERMINATION OF ANTIBODIES

[75] Inventors: Urban Schmitt, Oberhausen; Wolfgang Rüdinger, Birkenau; Gertraud Ehrlich-Weinreich, Gräfelfing, all of Fed. Rep. of Germany

[73] Assignee: Boehringer Mannheim GmbH, Mannheim-Waldhof, Fed. Rep. of Germany

[21] Appl. No.: 663,759

[22] Filed: Mar. 1, 1991

Related U.S. Application Data

[63] Continuation of Ser. No. 376,706, Jul. 7, 1989, abandoned.

[30] Foreign Application Priority Data

Jul. 8, 1988 [DE] Fed. Rep. of Germany ....... 3823262
Mar. 9, 1989 [DE] Fed. Rep. of Germany ....... 3907651

[51] Int. Cl.⁵ ................. G01N 33/543; G01N 33/564; C12Q 1/00; C07K 13/00
[52] U.S. Cl. .................................... 436/518; 436/507; 435/7.1; 435/7.93; 530/300; 530/387.1; 530/403; 530/810; 530/866
[58] Field of Search ................. 436/518; 435/507, 7.1, 435/7.93; 530/300, 387.1, 403, 810, 866

[56] References Cited

U.S. PATENT DOCUMENTS

| 4,659,678 | 4/1987 | Forrest et al. | 436/512 |
| 4,661,444 | 4/1987 | Li | 435/7 |
| 4,752,638 | 6/1988 | Nowinski et al. | 525/54.1 |
| 4,792,527 | 12/1988 | Uchida et al. | 436/507 |
| 4,870,007 | 9/1989 | Smith-Lewis | 435/28 |

FOREIGN PATENT DOCUMENTS 0245926 11/1987 European Pat. Off.
2084317 4/1982 United Kingdom.

Primary Examiner—Esther L. Kepplinger
Assistant Examiner—Bradley L. Sisson
Attorney, Agent, or Firm—Felfe & Lynch

[57] ABSTRACT

For the determination of antibodies based on an immunoassay technique by incubation with at least three receptors $R_1$, $R_2$ and $R_3$ which are present dissolved in a liquid phase and of which $R_1$ is an antigen which is capable of being specifically bound to the antibody to be determined, $R_2$ mediates the binding to the solid phase and $R_3$ carries a label, separation of the complex which forms from the solution by binding to a solid phase and measurement of the label in one of the phases, a conjugate is used as the receptor $R_2$ composed of a receptor capable of specific binding to $R_1$ and a substance $S_1$, which can be specifically bound, and a conjugate of a receptor which can specifically bind to $R_1$ and a label is used as $R_3$, wherein the immobilization of the complex which forms is mediated by binding to a component of the solid phase which can specifically bind $S_1$.

11 Claims, 2 Drawing Sheets

PROCESS FOR THE DETERMINATION OF ANTIBODIES

This application is a continuation of application Ser. No. 376,706, filed Jul. 7, 1989, now abandoned.

DESCRIPTION

The invention concerns a process for the determination of antibodies by incubation with at least three receptors $R_1$, $R_2$ and $R_3$ which are present dissolved in a liquid phase and of which $R_1$ is an antigen which is capable of being specifically bound to the antibody to be determined, $R_2$ mediates the binding to the solid phase and $R_3$ carries a label, separation of the complex which forms from the solution by binding to a solid phase and measurement of the label in one of the phases as well as a suitable reagent therefor.

Antibodies are protein molecules which are produced by B-lymphocytes and plasma cells on contact with the corresponding antigen and which are specifically directed against the antigen which triggered their formation. On the one hand, the body forms antibodies in response to invasion by exogenous molecules such as foreign proteins, bacteria or viruses and, on the other hand, when an auto-immune disease is present antibodies are formed against the body's own cells. The determination of specific antibodies therefore allows the diagnosis of the course of diseases or the presence of an auto-immune disease.

Antibodies can be detected sensitively by procedures based on immunoassays. Many variants of these are known such as competitive, immunoradiometric and immunoenzymometric assays as well as sandwich assays. Different variants are listed for example in an article by A. H. W. M. Schuurs and B. K. van Weemen in Dt. Ges. f. Klin. Chemie e.V.-Mitteilungen 1/79. In all variants, with the exeption of the competitive variant, a substance must be bound to a solid phase which reacts specifically with the antibodies to be determined. This substance can either be an antigen or hapten which reacts specifically with the antibody to be determined or it can also be an antibody directed against the antibody to be determined such as for example class-specific antibodies. A disadvantage of these described methods is that a specific solid phase has to be provided for each test.

Furthermore, a test procedure is described in the publication quoted above in which an antibody, directed against the class of antibodies to which the antibody to be detected belongs, is bound to a solid phase. In the presence of this solid phase the sample solution, containing the antibody to be determined, is incubated with a specific antigen for this antibody and with a labelled antibody which is likewise capable of binding to the antigen. During this process the antibody to be determined and the labelled antibody compete for binding to the antigen. Preformed immunocomplexes in the homogeneous phase which still have free antibody valencies are immobilized by the antibody bound to the solid phase and detected. Since the kinetics of binding to the solid phase is much slower than the kinetics of immunocomplex formation in the liquid phase, the solid phase binding does not proceed on a competitive basis but rather as a titration reaction. This method is however not sensitive enough for the detection of antibodies that are present in small amounts in the sample. The amount of specific antibodies necessary to perform this assay is very large.

The object of the present invention was therefore to provide a process by which antibodies can be detected sensitively by a simple method, wherein the amount of antibodies required can be reduced.

This object was achieved by a process for the determination of antibodies based on an immunoassay technique by incubation with at least three receptors $R_1$, $R_2$ and $R_3$ which are resent dissolved in a liquid phase and of which $R_1$ is an antigen or anti-idiotype-antibody which is capable of being specifically bound to the antibody to be determined, $R_2$ mediates the binding to the solid phase and $R_3$ carries a label, separation of the complex which forms from the solution by binding to a solid phase and measurement of the label in one of the phases, which is characterised in that a conjugate composed of a receptor capable of specifically binding to $R_1$ and a substance $S_1$, which can be specifically bound, is used as the receptor $R_2$ and a conjugate of a receptor which can specifically bind to $R_1$ and a label is used as $R_3$, whereby the immobilization of the complex which forms is mediated by binding to a component of the solid phase which can specifically bind to $S_1$.

Use of the process according to the present invention succeeded surprisingly in significantly improving the sensitivity. In addition, a much smaller amount of antibodies is required to perform this process.

In the process according to the present invention, the sample containing the antibody to be determined is incubated with three receptors which are all present dissolved in a liquid phase. Receptor $R_1$ is an antigen capable of being specifically bound to the antibody to be determined. Receptor $R_2$ is capable of specific binding to $R_1$ and mediates the binding to the solid phase for which it is appropriately derivatized. Receptor $R_3$ is likewise capable of specific binding to $R_1$ and carries in addition a label. In the sample solution receptor $R_2$ and receptor $R_3$ now compete together with the antibody to be determined for binding to the receptor $R_1$. The more antibody present in the sample, the more antibody that will also be bound to $R_1$ and the fewer binding sites that will be available for the receptors $R_2$ and $R_3$. Depending on the number of epitopes which the antigen exhibits, complexes form between $R_1$ and $R_2$, $R_3$ and/or the antibody to be determined. Only those complexes containing at least one receptor $R_2$ can be bound to the solid phase and only those complexes in which at least one receptor $R_3$ is bound participate in the indicator reaction. The complexes which form from receptor $R_1$, receptor $R_2$ as well as, according to the situation, receptor $R_3$ and/or the antibody to be determined are then bound to the solid phase by the substance $S_1$, capable of being specifically bound, which is bound in receptor $R_2$. In this process the binding can either result directly via components fixed to the solid phase which can specifically bind to $S_1$ or via components which mediate binding to the solid phase. After separation of the solid phase from the liquid phase the label can be determined in one of both phases, whereby the smaller the proportion of antibody to be determined in the sample solution the more bound label can be detected In the process according to the present invention $R_1$ is a receptor capable of being specifically bound to the antibody and has at least two epitopes recognizing the antibody. The receptor $R_1$ can be an antigen or an anti-idiotype-antibody.

According to the present invention a conjugate is used as receptor $R_2$ which consists of a receptor which specifically bind to $R_1$ and a substance $S_1$ capable of being specifically bound. The portion which specifically bind to $R_1$ serves to binds to the antigen employed and is an antibody or a fragment of an antibody. The substance $S_1$, which can be specifically bound, mediates the binding to the solid phase. For this purpose, the substance $S_1$, is preferably one partner of a specific binding pair. Such binding pairs are known to the expert. The following binding pairs are suitable; antigen-antibody; hapten-antibody; biotin-avidin/streptavidin; protein-antiprotein; protein A-immunoglobulin; hemoglobin-haptoglobin or enzyme-substrate. It is preferable to use a hapten as $S_1$ such as: digoxin, p-nitrophenol, saponin, FITC and, in particular, biotin. The binding of $S_1$ to the receptor which specifically binds to $R_1$ is carried out according to a known procedure. Methods for this purpose are known to the expert.

The third receptor used is a conjugate of a receptor which can specifically bind to $R_1$ and a label. An enzyme, a radioactive substance, an isotope, or a fluorescent or chemiluminescent substance can be used for labelling; the determination of these labels is performed by methods well known to the expert. The conjugate is prepared according to known methods.

The receptors, capable of specifically binding which are used for the receptors $R_1$ and $R_2$ are antibodies or their fragments which can bind to the antigen used for receptor $R_1$. Since these receptors, capable of specific binding, should compete with the antibody to be determined for binding to the antigen, it is essential that one uses receptors which react with the antigen in a similar way to the antibody to be detected i.e. they should have a similar binding capacity. Therefore, either polyclonal antibodies are used for each of the receptors $R_2$ and $R_3$ which have the same binding capability as the antibody to be detected, or it is just as possible to use a monoclonal antibody if it can be ensured that the epitope on the antigen recognised by this monoclonal antibody is also recognized by the antibody to be determined.

Both of the receptors $R_2$ and $R_3$ have to be employed in such a proportion that, on the one hand, sufficient receptors $R_2$ can bind to $R_1$ to ensure immobilization of the complexes which form and, on the other hand, sufficient receptors $R_3$ are bound since detection is only possible by means of the label.

The immobilization of the complex which forms from antigen, $R_2$, $R_3$ and/or the antibody to be determined on a solid phase is mediated by the substance $S_1$ capable of being specifically bound. There are two alternatives for this. In a preferred embodiment components are bound to the solid phase which can specifically bind to $S_1$. For this purpose the complementary partner to $S_1$ of the specific binding pair is bound to the solid phase in a known way. The competitive reaction of the receptors $R_2$, $R_3$ and the antibody to be determined with $R_1$ is not interfered with, even when the incubation takes place in the presence of the solid phase, because the reaction of the receptors $R_1$, $R_2$ and $R_3$ takes place in a homogeneous phase and thus proceeds much more quickly than binding to the heterogeneous phase. It is of course equally possible to carry out the complex formation first and then to add the solid phase after the addition of which binding to the wall can then take place. As a solid phase, polymer materials as well as cellulose-containing materials or glass are suitable. Polystyrene, polymethacrylate, teflon, polyamide, copolymers of styrene and acrylonitrile, glass and cellulose products have proven to be particularly suitable. The solid phase can be present in a variety of forms such as tubes, microtitre plates, spheres, film, powder, granules or fibre-pad.

The said component, capable of specific binding, can be bound to the solid phase in a known manner. The binding can either be directly to the solid phase or via a spacer or a binding protein. Processes for this purpose are known to the expert. The process for the production of a solid phase matrix described in the patent application DE-A 36 40 412 is for example suitable.

In a further preferred embodiment of the process according to the present invention a second substance $S_2$, capable of being specifically bound, is bound to the solid phase. This substance $S_2$ is, like $S_1$, a partner of a specific binding pair as defined above. It is particularly preferable if $S_1$ and $S_2$ are identical. For immobilization a component is then added which has at least one specific binding site for each of $S_1$ and $S_2$. This component can be a molecule which has two or more binding sites for $S_1$ and $S_2$ respectively, it can also be a conjugate of two different molecules each of which possesses a specific binding site for $S_1$ and $S_2$ respectively. Furthermore, it is possible to employ the said component in cross-linked form i.e. polymers of substances capable of binding to $S_1$ and $S_2$ respectively. It is particularly preferable to use biotin as $S_1$ and $S_2$. For the immobilization, avidin or streptavidin can then be used which can be present either in a monomeric or polymeric form.

By addition of the said component to the solution the conjugate formed from antigen and $R_2$, $R_3$ and/or the antibody to be determined is fixed to the solid phase via binding of the said component to $S_1$ and via binding of the said component to $S_2$. The phases can then be easily separated by removing the liquid. After separation of the phases the label can be determined in one of the two phases according to known methods and is a measure of the amount of antigen-specific antibody.

The process according to the present invention is simple to perform since it can be carried out in one or at most two steps. It is therefore also possible to apply this process on an automated analyser. Since the process proceeds competitively the amount of antibody necessary can be considerably reduced in comparison to the frequently used methods of determination of the prior art since the latter are all in the form of sandwich-techniques or immunometric methods. Nevertheless, very good results are obtained with the process according to the present invention in which the sensitivity could be improved even further in comparison to the known methods.

A further embodiment of the present invention is a reagent for the determination of antibodies containing receptors $R_1$, $R_2$ and $R_3$ as well as a solid phase which are physically separated from one another, wherein $R_1$ is an antigen capable of being specifically bound to the antibody to be determined, $R_2$ is a conjugate of a receptor which specifically binds to $R_1$ and a substance $S_1$ which can be specifically bound and $R_3$ is a conjugate of a receptor which specifically binds to $R_1$ and a label.

For the reagent according to the present invention, it is preferred to use a solid phase on which a component is bound which can specifically bind to $S_1$. Immobilization via the specific binding pair biotin-avidin/streptavidin is especially preferred.

Equally preferred is the use of a solid phase on which a second substance $S_2$, capable of being specifically bound, is bound, wherein the reagent contains in addition a component which has at least one specific binding site for each of $S_1$ and $S_2$. Preferably the same substance, capable of being specifically bound, is bound on the solid phase as that which is bound in receptor $R_2$. Also in this embodiment it is particularly preferable to use biotin and avidin/streptavidin as the binding pair.

The invention is elucidated by the following figures and examples.

Figure 1:
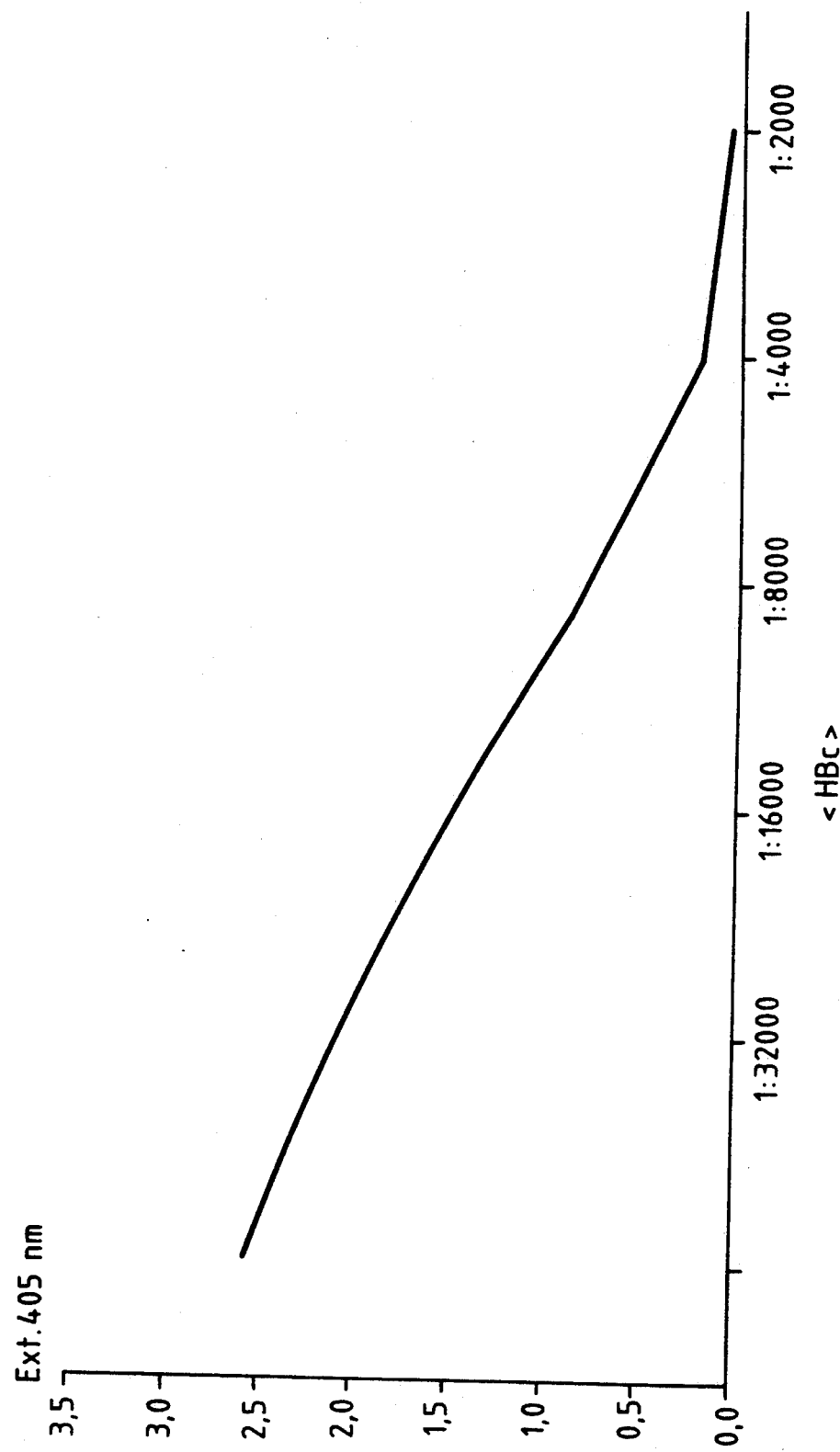
FIG. 1 shows a calibration curve for a determination of antibodies against HBcAG using the process according to the present invention.

The monoclonal antibody against HBcAG referred to in the examples is deposited at the European Collection of Animal Cell Cultures under the following number: ECACC 88022507.

EXAMPLE 1

Receptors $R_2$ and $R_3$ were prepared for the determination of antibodies against HBcAG.

a) Preparation of a conjugate of a monoclonal antibody against HBcAG (Hepatitis B-Core-Antigen) and biotin.

6 mg/ml D-biotin-ε-aminocaprylic acid-n-hydroxysuccinimide ester was first dissolved in dimethylsulphoxide. Then 10 mg/ml antibody in 30 mmol/l potassium phosphate buffer, pH 7.5, was incubated for one hour at 25° C. with a fifteenfold molar excess of biotinylation reagent and then dialysed against 2 mmol/l potassium phosphate buffer, pH 7.5.

b) Conjugate of a monoclonal antibody against HBcAG (ECACC 88022507) and peroxidase.

Horseradish-peroxidase was oxidized according to the periodate method described by Nakane (Wilson, M. B., Nakane, P. K. "Immunofluorescence and Related Staining Techniques" W. Knapp, Holuber and G. Wick, published by Elsevier/North-Holland Biomedical Press Amsterdam New York 1978, pages 215 to 224). 10 mg antibody and 12 mg oxidized peroxidase were then coupled together in a total volume of 4.6 ml at 25° C. and a pH of 9.4. The cross-linking was stopped after one hour by addition of 20 mmol/l triethanolamine and 1.5 mmol/l sodium borhydride and incubation (for 30 minutes) at 0° C. and pH 8.9. Afterwards the conjugate was fractionated by gel-filtration on Superose 6 prep. grade in 50 mmol/l potassium phosphate buffer, pH 7.5 and 150 mmol/l NaCl.

EXAMPLE 2

The amount of antibody against Hepatitis B-Core-Antigen in human serum was determined. The following reagents were used for this:

Reagent 1: 100 ng/ml recombinant HBcAG (prepared according to EP-A 0013828)

Reagent 2: 50 ng/ml biotinylated monoclonal antibodies against HBcAG (ECACC 88022507), prepared according to Example 1a and conjugate of monoclonal antibodies against HBcAG and peroxidase (prepared according to Example 1b, POD-activity 25 mU/ml) in 40 mmol/l sodium phosphate buffer, pH 7.4
0.5% polyether glycol ( Pluronic F-68)
0.2% bovine serum albumin
0.1% bovine IgG
0.2 mol/l sodium tartrate.

200 μl of sample was pipetted into a polystyrene tube coated with streptavidin-thermo-bovine serum albumin, prepared as described in DE-A 36 40 412, and 500 μl of reagent 1 and reagent 2 were added either in quick succession or, alternatively, simultaneously. After incubation for one hour at room temperature the tube was washed three times with tap water and 1 ml ABTS (2,2'-azino-di-[3-ethyl-benzthiazoline-(6)-sulphonic acid]-diammonium salt) (1.9 mmol/l) was pipetted into the tube for the substrate reaction and incubated for a further hour at room temperature. The absorbance was measured at 405 nm in a cuvette with a 5 mm path length and converted to the corresponding reading for a 1 cm cuvette.

FIG. 1 shows a calibration curve which was obtained by diluting a positive with a negative serum. The absorbance readings are summarised in Table 1.

TABLE 1

| Dil. HBc | Example 2 Abs.$_{405\,nm}$ | Example 3 Abs.$_{405\,nm}$ |
|---|---|---|
| 1:2000 | 0.048 | 0.040 |
| 1:4000 | 0.195 | 0.803 |
| 1:8000 | 0.792 | 1.856 |
| 1:16000 | 1.489 | 2.565 |
| 1:32000 | 2.070 | 2.767 |
| Neg. serum | 2.570 | 2.845 |
| Detection limit | 1.050 | 1.225 |

EXAMPLE 3 (COMPARISON)

For the purpose of comparison antibodies against HBcAG were determined by a prior art method. For this purpose polystyrene tubes were filled with 1.5 ml of a solution containing 3 μg/ml monoclonal antibody against HBcAG (ECACC 88022507) in 40 mmol/lphosphate buffer, pH 7.4 and left to stand for 24 hours at room temperature. After removal of the solution the tubes were filled with 2 ml buffer consisting of 0.9% NaCl, 0.3% bovine serum albumin and 2% saccharose and incubated for half an hour. After removal of these solutions the tubes were inverted and incubated over night in this position at 21° C. The further procedure was as described in Example 2 except that instead of the streptavidin-thermo-BSA coated polystyrene tubes a polystyrene tube coated with monoclonal antibodies against HBcAG was used and reagent 2 was prepared without biotinylated monoclonal antibody against HBcAG.

Figure 2:
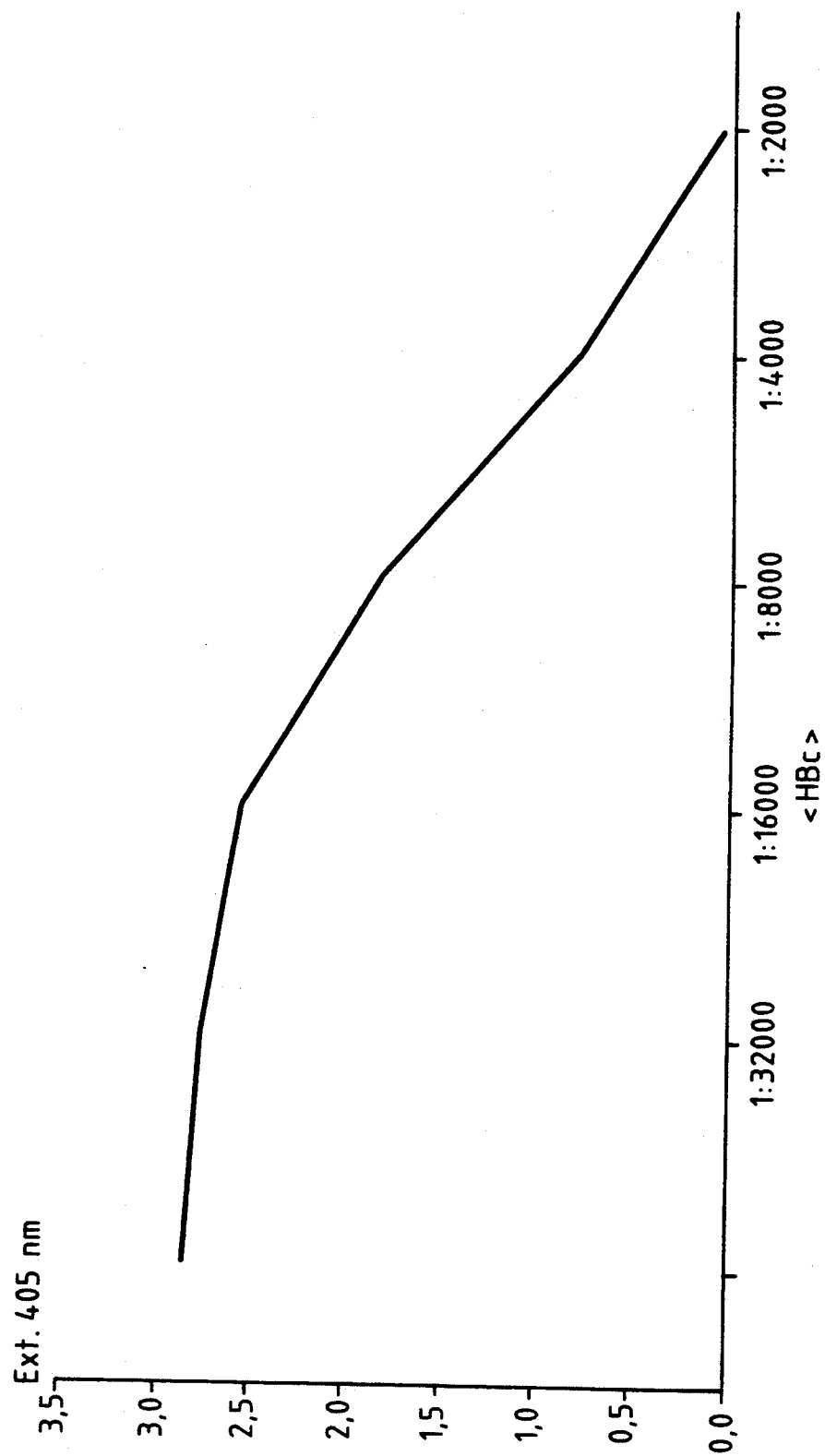
FIG. 2 shows a calibration curve for a determination of antibodies against HBcAG according to the prior art.

The results are shown in Table 1. FIG. 2 shows a calibration curve which was obtained by diluting a positive with a negative serum.

EXAMPLE 4

A competitive test was carried out to determine antibodies against Hepatitis B-Core-Antigen in serum. For this purpose 500 μl of a reagent consisting of:
  50 ng/ml biotinylated monoclonal antibodies against HBcAG (ECACC 88022507), which was prepared according to example 1a (receptor $R_2$),
  100 ng/ml recombinant HBcAG which was prepared according to the instructions described in EP-A 0013828 (receptor $R_2$) and
  200 μl sample
were pipetted into polystyrene tubes coated with streptavidin-thermo-bovine serum albumin (prepared as described in Example 2) and incubated in a solution containing 40 mmol/l sodium phosphate buffer, pH 7.4, 0.5% polyether glycol (Pluronic F-68), 0.2% bovine serum albumin, 0.1% bovine-IgG and 0.2 mol/l sodium tartrate. After incubation for one hour at room temperature 500 μl of a second reagent was added containing the conjugate of monoclonal antibody against HBcAG and peroxidase in the buffer solution described above, obtained according to Example 1b (receptor $R_3$), with a peroxidase activity of 25 mU/ml and incubated for a further hour. After completion of the incubation the tubes were washed three times with tap water and 1 ml of ABTS (1.9 mmol/l) was pipetted for the substrate reaction and incubated for one hour at room temperature. The absorbance was measured at 405 nm in a cuvette with an path length of 5 mm and converted to the corresponding reading for a 1 cm cuvette.

The absorbance readings are summarised in Table 2.

EXAMPLE 5

For the determination of antibodies against Hepatitis-B-Core-Antigen by a competitive method 200 μl sample and 500 μl Reagent 1 consisting of 100 ng/ml recombinant HBcAG (prepared according to EP 0013828) in 40 mmol/l sodium phosphate buffer, pH 7.4, 0.5% polyether glycol (Pluronic F-68), 0.2% bovine serum albumin, 0.1% bovine IgG, 0.2 mol/l sodium tartrate were pipetted into a polystyrene tube coated with streptavidin-thermo-bovine serum albumin (prepared as described in DE-A 3640412). After incubation for one hour 500 μl of Reagent 2 consisting of:

50 ng/ml biotinylated monoclonal antibodies against HBcAG (prepared according to Example 1a) and
25 mU/ml conjugate of monoclonal antibodies against HBcAG and peroxidase (prepared as described in Example 1b)

was added in a buffer solution, as described above for Reagent 1, and incubated for a further hour at room temperature.

The further procedure was as described for Example 3.

The absorbance readings obtained are summarised in Table 2.

TABLE 2

| Anti-HBc positive-serum Dilution | Example 4 Abs.405 nm | Example 5 Abs.405 nm |
|---|---|---|
| 1:2000 | 0.075 | 0.016 |
| 1:4000 | 0.163 | 0.046 |
| 1:8000 | 0.357 | 0.229 |
| 1:16000 | 0.637 | 0.563 |
| 1:32000 | 0.907 | 0.814 |
| Neg. serum | 1.165 | 1.206 |
| Detection limit | 0.491 | 0.493 |

We claim:

1. Method for the determination of an antibody is an aqueous antibody containing sample solution comprising incubating said aqueous, antibody containing sample solution with at least three receptors $R_1$, $R_2$ and $R_3$ which are present dissolved in a liquid phase, where $R_1$ is a receptor which specifically binds to the antibody to be determined, $R_2$ is a conjugate of a receptor which specifically binds to $R_1$, and a substance $S_1$ which is a member of a specific binding pair, and $R_2$ binds to a solid phase via $S_1$ and $R_3$ is a conjugate of a receptor which specifically binds to $R_1$ and a label, under conditions favoring formation of complexes containing $R_1$ and at least one of said antibody, $R_2$, and $R_3$, and formation of solid phase bound complexes containing $R_2$, separating the solid phase bound complexes from the solution and measuring the label in one of said phases as a determination of said antibody.

2. Method of claim 1, wherein all three receptors are added to the sample aqueous, antibody containing sample simultaneously.

3. Method as claim 1, wherein receptors $R_2$ and $R_3$ have the same binding capacity as the antibody to be determined.

4. Method of claim 1, wherein the receptor of both of $R_2$ and $R_3$ is a polyclonal antibody which specifically binds to $R_1$.

5. Method of claim 1, wherein $S_1$ and the component to which it binds on the solid phase are selected from the group of pairs consisting of antigen-antibody; hapten-antibody; protein-antiprotein; protein-A-immunoglobulin; hemoglobin-haptoglobin; enzyme-substrate avidin-biotin and streptavidin-biotin.

6. Method of claim 1, wherein $R_2$ and $R_3$ comprise monoclonal antibodies or fragments of monoclonal antibodies which bind to $R_1$.

7. Method of claim 1, comprising sequentially incubating said aqueous, antibody containing sample with at least $R_1$ in a first step, and incubating said aqueous, antibody containing sample with $R_2$, $R_3$ or a mixture of $R_2$ and $R_3$ in a second step, wherein the receptor incubated in the second step have not been incubated in the first step.

8. Method of claim 1, wherein said solid phase has bound thereto a second member of a specific binding pair which binds to $S_1$.

9. Method of claim 1, wherein said solid phase has bound thereto a second substance $S_2$ which specifically binds to a second member of a specific binding pair which also binds to $S_1$, said method further comprising incubating said three receptors $R_1$, $R_2$ and $R_3$, said solid phase and said sample solution, followed by incubation with said second member of a specific binding pair.

10. Method of claim 9, wherein $S_1$ and $S_2$ are identical to each other.

11. Method of claim 10, wherein $S_1$ and $S_2$ are biotin, and said second member of a specific binding pair is avidin or streptavidin.

* * * * *